(12) United States Patent
Summers

(10) Patent No.: US 7,504,665 B2
(45) Date of Patent: Mar. 17, 2009

(54) SEMICONDUCTOR OPTICAL DEVICES

(75) Inventor: Huw David Summers, Cardiff (GB)

(73) Assignee: University College Cardiff Consultants, Ltd., Cardiff (GB)

(*) Notice: Subject to any disclaimer, the term of this patent is extended or adjusted under 35 U.S.C. 154(b) by 195 days.

(21) Appl. No.: 10/532,363

(22) PCT Filed: Oct. 22, 2003

(86) PCT No.: PCT/GB03/04558
§ 371 (c)(1), (2), (4) Date: Sep. 28, 2005

(87) PCT Pub. No.: WO2004/038813
PCT Pub. Date: May 6, 2004

(65) Prior Publication Data
US 2006/0138434 A1 Jun. 29, 2006

(30) Foreign Application Priority Data
Oct. 22, 2002 (GB) ............... 0224503.3
Jan. 9, 2003 (GB) ............... 0300434.8

(51) Int. Cl.
H01L 27/15 (2006.01)
(52) U.S. Cl. .............. 257/82; 257/80; 257/84; 257/88; 257/98; 257/436; 257/464; 257/E51.021
(58) Field of Classification Search ............... 257/80, 257/82, 84, 88, 98, 436, 464, E51.021
See application file for complete search history.

(56) References Cited

U.S. PATENT DOCUMENTS

| 5,319,182 | A | | 6/1994 | Havens et al. |
| 5,533,041 | A | | 7/1996 | Mastuda et al. |
| 5,606,572 | A | * | 2/1997 | Swirhun et al. .............. 372/96 |
| 5,679,964 | A | | 10/1997 | Kobayashi et al. |
| 5,877,519 | A | * | 3/1999 | Jewell ..................... 257/190 |
| 5,978,401 | A | | 11/1999 | Morgan |
| 6,370,176 | B1 | | 4/2002 | Okumura |
| 2001/0046712 | A1 | | 11/2001 | Hang et al. |

FOREIGN PATENT DOCUMENTS

JP 57173984 10/1982
WO WO 01/26102 4/2001

* cited by examiner

Primary Examiner—Evan Pert
Assistant Examiner—Tan N Tran
(74) Attorney, Agent, or Firm—Gordon & Jacobson, PC

(57) ABSTRACT

A semiconductor optical device (e.g. a resonant cavity device in this form of an LED or a laser) comprises a single substrate arranged for emitting light (O) for incidence on a sample or other element and also responsive to light (D), e.g. of a different wavelenght, received back from this sample or other element: the device further comprises means for monitoring a characteristic (e.g. its current-voltage characteristic) which varies in dependence upon the light (D) received back from the sample or other element.

17 Claims, 8 Drawing Sheets

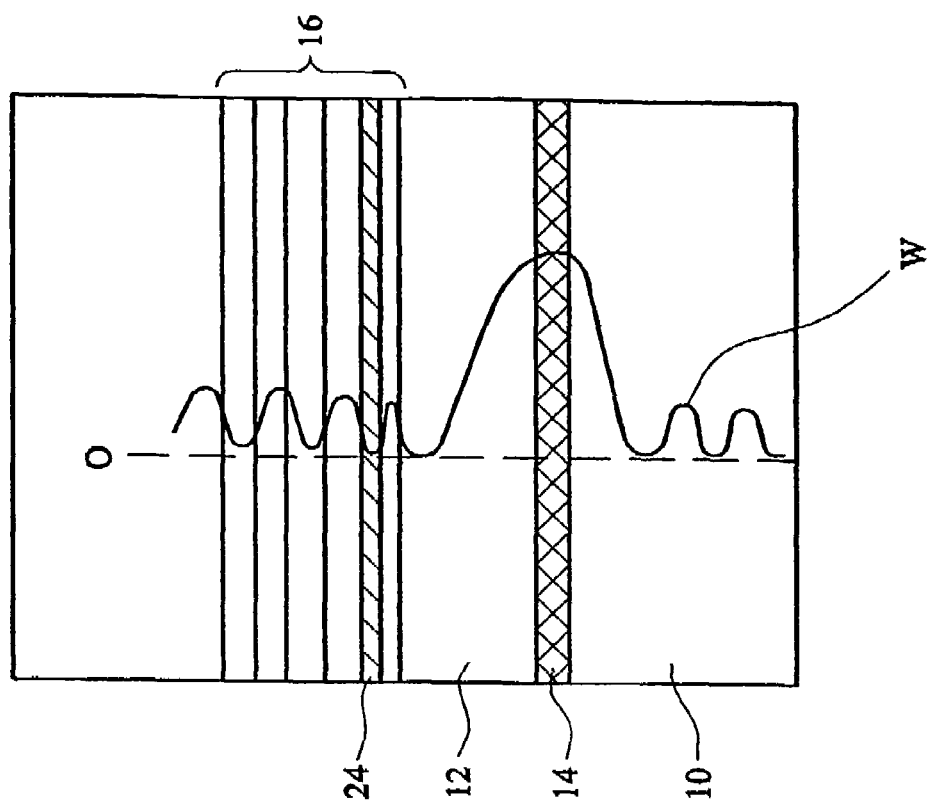
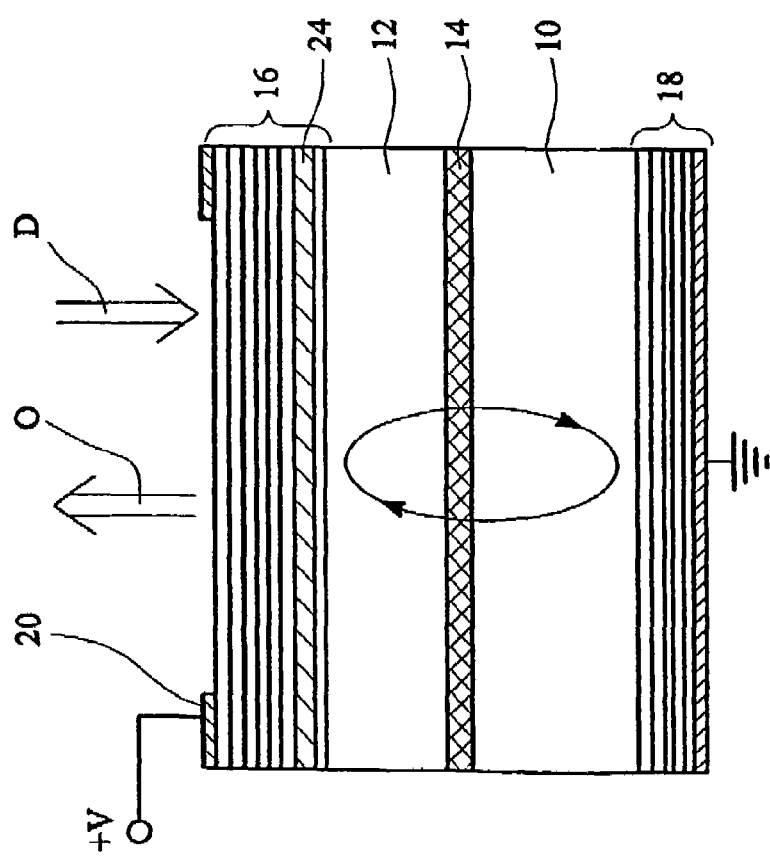
FIG. 3
FIG. 2

SEMICONDUCTOR OPTICAL DEVICES

BACKGROUND OF THE INVENTION

1. Field of the Invention

The present invention relates to semiconductor optical devices, particularly but not solely for use in the field of bio-chemical or bio-medical analysis.

2. State of the Art

The use of optical techniques for the analysis of biological samples is a field of increasing importance, particularly in view of its potential for analysis at a molecular level. Various optical systems have been proposed hitherto: these systems have generally made use of a laser or other light emitter for directing light onto samples, typically successive samples in an array, and a separate photodetector for picking up light from the individual samples; typically the samples have been marked with a fluorescent dye, such that the incident light stimulates each sample to cause the emission of light of a different wavelength, which is picked up by the photodetector. Hitherto, such systems have been of large and complicated construction, for laboratory use.

SUMMARY OF THE INVENTION.

We have now devised semiconductor optical devices which provide both light emission and light detection, for example enabling integration of an analytical system and providing a number of consequent advantages, but also of potential use in other applications: the devices may be of simple and small construction, enabling them to be used in the field.

In accordance with the present invention as seen from one aspect, there is provided a semiconductor emitter/detector optical device comprising a single substrate arranged for emitting light for incidence on a sample or other element and also responsive to light received from said sample or other element, the device further comprising means for monitoring a characteristic of the device which varies in dependence upon said light received from said sample or other element.

The device may include a photodetector, integrated on its substrate, for responding to the received light and providing an electrical output signal depending thereon. The photodetector may respond to received light of the same wavelength as the light emitted by the device, for example reflected from a sample or other element, and/or it may respond to received light of a different wavelength, for example light emitted by a sample in response to stimulation by the light emitted by the device: such stimulated light emission may be produced by fluorescence.

Instead, the device may be such that the received light affects an electrical property of the device and so alters its current-voltage or impedance characteristic. In this case the monitoring means is arranged to monitor the current-voltage characteristic of the device, which varies depending on the received light (particularly the intensity thereof).

The device may comprise an array of light emitter/detectors integrated on the common substrate, these light emitter/detectors operating independently of each other and the monitoring means being arranged for monitoring the relevant device characteristic in respect of each emitter/detector, independently of the others. The device may then be used for performing an analytical test on a plurality of samples, one for each light emitter. The device preferably comprises a surface-emitting device, with an array of surface regions emitting light from the corresponding array of emitters, for the samples to be positioned in a similarly corresponding array over that surface. For example, a second substrate may be disposed over the device surface, this second substrate being formed with an array of recesses or chambers or flow ducts for receiving respective samples. The second substrate may be integrated with the device, or it may comprise a separate component. The plurality of light emitter/detectors may be arranged in a two-dimensional array, or in a linear array.

The device preferably comprises a resonant cavity light emitting device, for example a resonant cavity LED or a laser, preferably a vertical-cavity, surface emitting laser (or VCSEL).

A secondary optical cavity may be disposed over the emitting surface of the device, to form a coupled-cavity system, the secondary cavity including a chamber or flow duct for a sample.

In the case of a resonant cavity device, preferably a reflector thereof, through which the light output is emitted, comprises a plurality of alternating layers of high and low refractive index materials, and a layer of absorbing material is incorporated into or associated with the reflector. This absorbing layer serves to absorb light of a wavelength different from (typically longer than) the light emitted by the device: in absorbing light, electron-hole pairs are generated in the absorbing layer, so altering the current-voltage characteristic of the device. Because of its position at a node of the optical standing wave within the resonant cavity, the absorbing layer does not affect the light emitted by the device.

It will be appreciated that electron-hole pairs are produced in the absorbing layer, when light is absorbed in this layer. We have found that it is necessary for an electric field to exist across the absorbing layer, so that these electrons and holes are removed and effectively contribute to the current flow. In order to ensure this condition, preferably the absorbing layer is positioned in an undoped semiconductor region of the device: the PN-junction of the device then produces the desired electric field across the absorbing layer. The absorbing layer may be positioned in an undoped semiconductor layer or region lying between two groups of alternating high and low refractive index materials which form the reflector through which the light output of the device is emitted.

The device may typically comprise a two-terminal, vertically integrated device, with the monitoring means arranged to monitor the current-voltage characteristic of the device. For example, a constant voltage source may be connected across the device and the monitoring means arranged to monitor the current flow: instead, the device may be fed from a constant current source and the monitoring means arranged to monitor the voltage across the device.

The monitoring means may comprise a circuit, part of which is integrated on the semiconductor substrate of the device.

The semiconductor substrate may comprise a light-emitting layer disposed centrally between upper and lower reflectors, to form a resonant cavity, which is accordingly resonant at the wavelength of the emitted light. Instead, the cavity may be resonant at the wavelength of light to be detected, being a wavelength different from the emitted light: in this case, the layer, which is absorbing to the light to be detected, is disposed centrally between upper and lower reflectors, and a light emitting layer is disposed adjacent the upper and/or lower reflectors.

The device in accordance with the present invention may comprise a light emitter element and a photodetector element, both integrated on a single substrate. The light emitter and/or photodetector may comprise a resonant cavity, in the form either of an LED or a laser. The photodetector may be arranged to detect light of a different wavelength from (e.g. of longer wavelength than) the light emitted by the light emitter:

in this case, preferably the photodetector is arranged to respond preferentially to light of the former wavelength, so that it is relatively immune to any emitted light reflected or scattered back to the photodetector. For example, the photodetector element may be provided with a filter layer, at or adjacent its surface, which transmits light of the wavelength to be detected but blocks light of the emitted wavelength: this filter layer may be provided in an upper reflector of the photodetector.

In one embodiment of device in accordance with the present invention, the semiconductor substrate is formed with a resonant cavity between upper and lower reflectors, but a region of the upper reflector is removed to form an emitter, whilst another region of the substrate forms a photodetector and includes a layer, in the upper reflector, which filters out reflected emitted light.

Preferably a reverse bias applied to the photodetector places the diode close to its breakdown point: thus, in use, avalanche photo-detection occurs, thus substantially increasing the detection signal.

Devices in accordance with the present invention may comprise at least one pair of light emitter/detectors, only one directing emitted light onto a sample or other element and receiving reflected or return light from that sample or other element, whilst the other emitter/detector acts as a reference: the detection output signals of the two emitter/detectors are then combined together in a manner to cancel the noise components of these signals.

It will be appreciated that the above-described devices in accordance with the present invention may be miniaturised and mass produced, to provide mass-produced devices which are inexpensive yet reliable. Moreover, the samples may be positioned very closely to both the light emitter region and the light receiving region of the device, providing for high detection efficiency. It is particularly advantageous to provide for independent testing by means of an array of emitters/detectors on the same device.

In accordance with the present invention as seen from a second aspect, there is provided a device for the analysis or testing of a biological sample, the device comprising a single light emitter for directing light onto a sample, and a single photodetector for receiving light from the sample.

This device is accordingly a single-channel device for use with a single sample (or a single sample at a time). The device may be constructed to a very small size and inexpensively, so that it can be used with ease in the field, and may indeed comprise a single use or disposable device.

The light emitter and photodetector may be mounted side-by-side and arranged for the biological sample to be positioned over them. The device may comprise a carrier substrate for the sample, positioned permanently or removably over the light emitter and photodetector.

Preferably the light emitter has a light emission peak at one wavelength and the photodetector has a light-absorbing peak at a different wavelength. In particular, the device may be arranged to detect fluorescent emission from the sample, stimulated by the light incident on it from the emitter.

The light emitter may comprise a vertical-cavity, surface emitting laser (VCSEL) or a resonant-cavity, light emitting diode (RCLED). The photodetector may comprise an identical device, having an emission peak at a different (longer) wavelength and used with a reverse bias, so as to act as a photodetector.

BRIEF DESCRIPTION OF THE DRAWINGS

Embodiments of the present invention will now be described by way of examples only and with reference to the accompanying drawings, in which:

FIG. 2 is a diagrammatic section through a semiconductor emitter/detector device forming a first embodiment of the present invention;

FIG. 3 is a section, on enlarged scale, of part of the device of FIG. 1, showing the optical intensity variation therein;

DETAILED DESCRIPTION OF THE PREFERRED EMBODIMENTS

Figure 1:
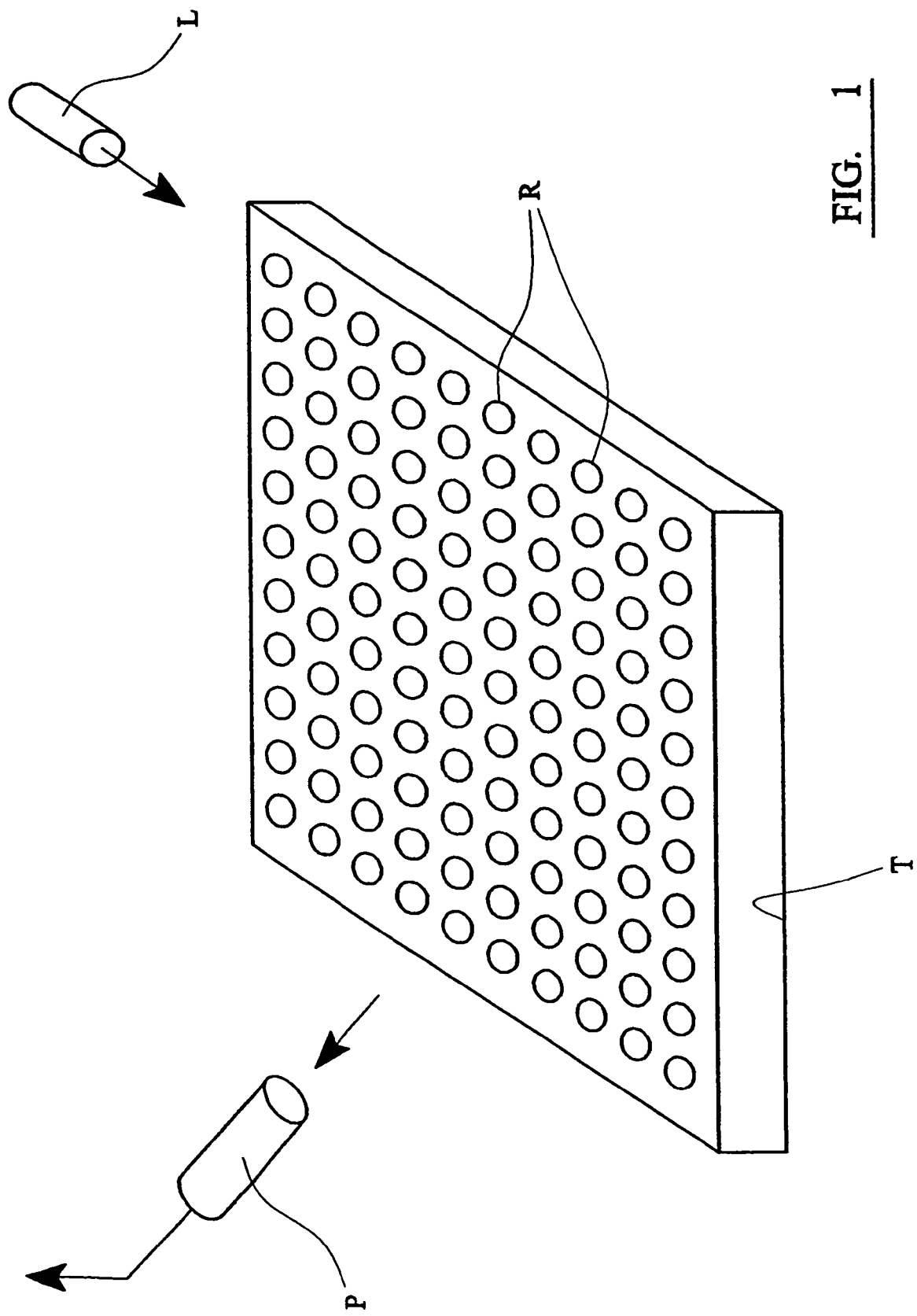
FIG. 1 is a schematic view of a prior art system for the optical analysis of biological samples.

Referring to FIG. 1, there is shown a prior art system for the optical analysis of an array of biological samples, each of the samples being marked with a fluorescent dye. The system comprises a tray T the upper surface of which is formed with a two-dimensional array of recesses or wells R which receive respective samples. A laser or other source S is provided to direct light onto the samples: means are provided for scanning the light beam onto the samples in succession. A photodetector P is provided to pick up the light emitted, by fluorescence, from the successive samples, the output of the photodetector being passed to a processing unit.

Referring to FIG. 2, there is shown a semiconductor device in accordance with the present invention in the form of a vertical-cavity, surface-emitting laser (or VCSEL), for use in performing an analytical test on a biological sample. The device comprises a semiconductor substrate having cavity layers 10,12 and an intermediate gain material layer 14, and upper and lower multi-layer reflectors 16,18: each reflector comprises a plurality of alternating layers of different materials, respectively of high and low refractive index, each layer being a ¼ wavelength thick. The device is provided with electrodes 20,22 on its top and bottom surfaces: in use, a voltage is applied between the upper and lower electrodes 20,22 to provide a current flow through the device; this current excites the device to cause lasing within its resonant cavity, the laser output light O being emitted through the top surface of the device.

In accordance with the present invention, the laser output is directed onto a biological or bio-chemical sample (not shown) positioned on or above the device, the sample being marked with a fluorescent dye. The laser output O stimulates the sample, causing the emission of light of a longer wavelength than the laser output light: some of the light D emitted from the sample returns and passes into the device.

The upper reflector 16 includes a layer 24 of narrow bandgap material, forming an absorbing layer for the light of the wavelength emitted by the sample. The absorbing layer 24 is disposed at a position which corresponds with a node in the internal optical standing wave of the device cavity: the variations in optical intensity are shown by the trace W in FIG. 3 and show the absorbing layer 24 at a node; accordingly, the absorbing layer 24 does not absorb the light emitted by the device or affect its lasing characteristics.

In use, the light D picked up by the device, from the sample, is absorbed by the absorbing layer 24, generating hole-electron pairs, which accordingly alter the current-voltage characteristic of the device. A constant voltage source may be connected across the device, and means provided to monitor the current flow, the current varying in dependence on the intensity of light D received from the sample. Alternatively, the device may be fed from a constant current source, and means provided to monitor the voltage across the device, which again varies in dependence upon the intensity of light D received from the sample.

Figure 4:
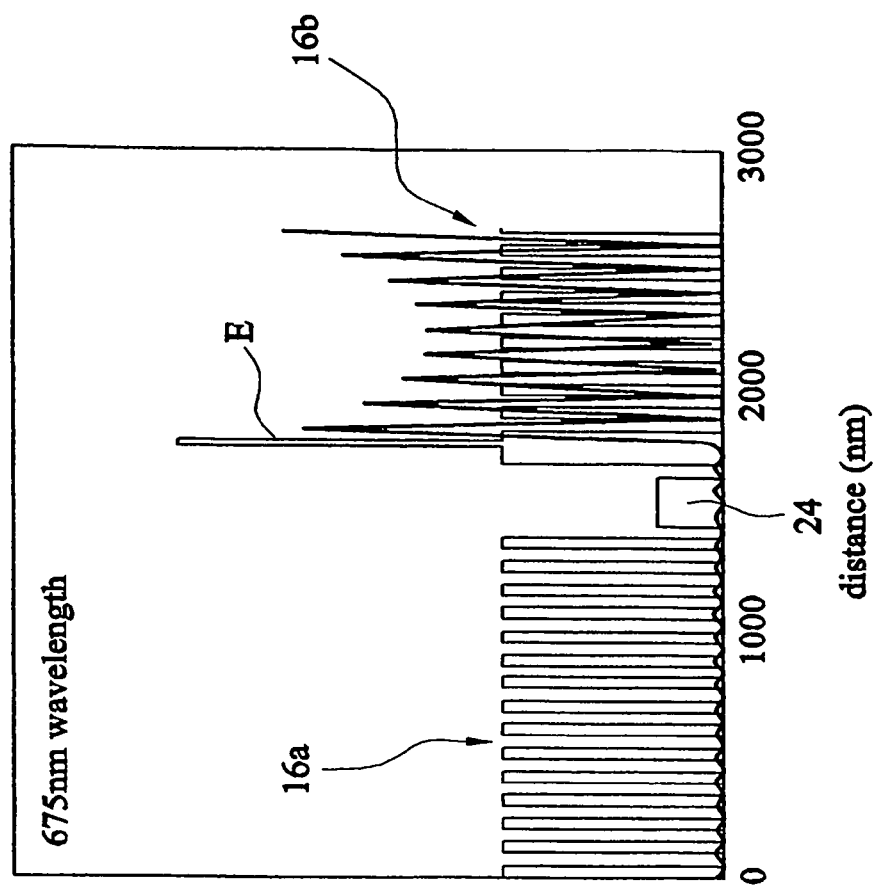
FIGS. 4 and 5 are graphs showing calculated electrical field profiles in the reflector which incorporates an absorbing layer.
Figure 5:
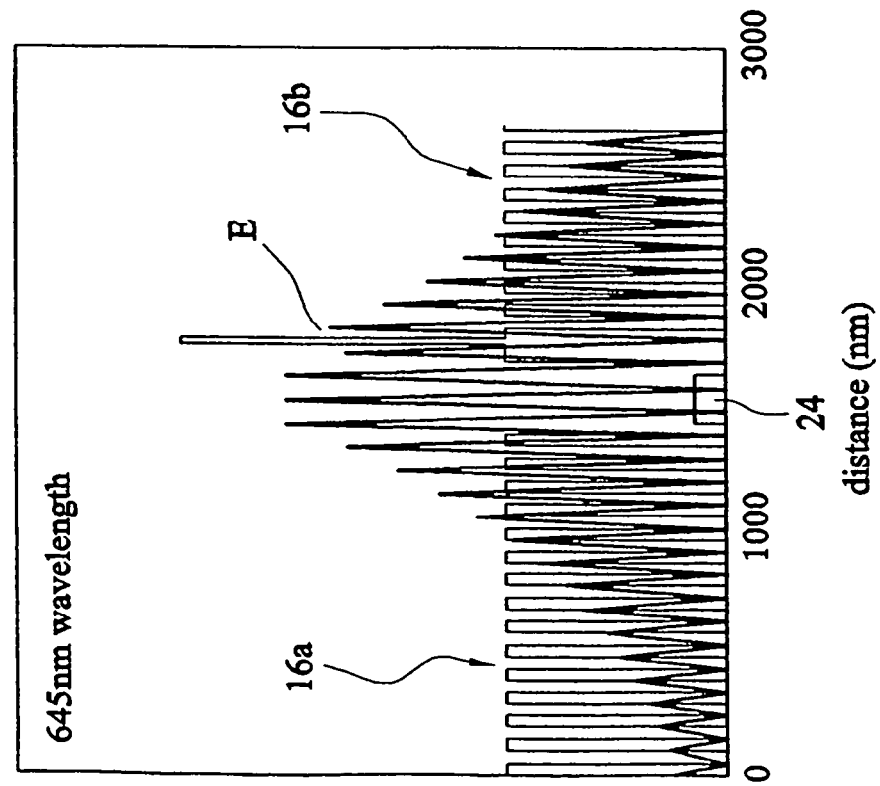

Referring in more detail to the structure of the upper reflector 16, in a preferred form this comprises a first group of alternating layers of high and low refractive index materials, then an undoped layer of semiconductor material, then a second group of alternating layers of high and low refractive index materials, with the absorbing layer disposed in the undoped layer between the two groups of alternating high and low refractive index layers. FIGS. 4 and 5 show the two groups of alternating high and low refractive index layers at 16a, 16b and the absorbing layer at 24, the distance being measured outwardly from the optical cavity of the device: the trace E shows the calculated electrical field. For the emitted light wavelength of 645 nm, the absorbing layer 24 is at a node or minimum in the electrical field and does not therefore affect the light being emitted by the device: for the returned light of 675 nm wavelength, this is no longer the case and the absorbing layer 24 serves to absorb this light.

Figure 6:
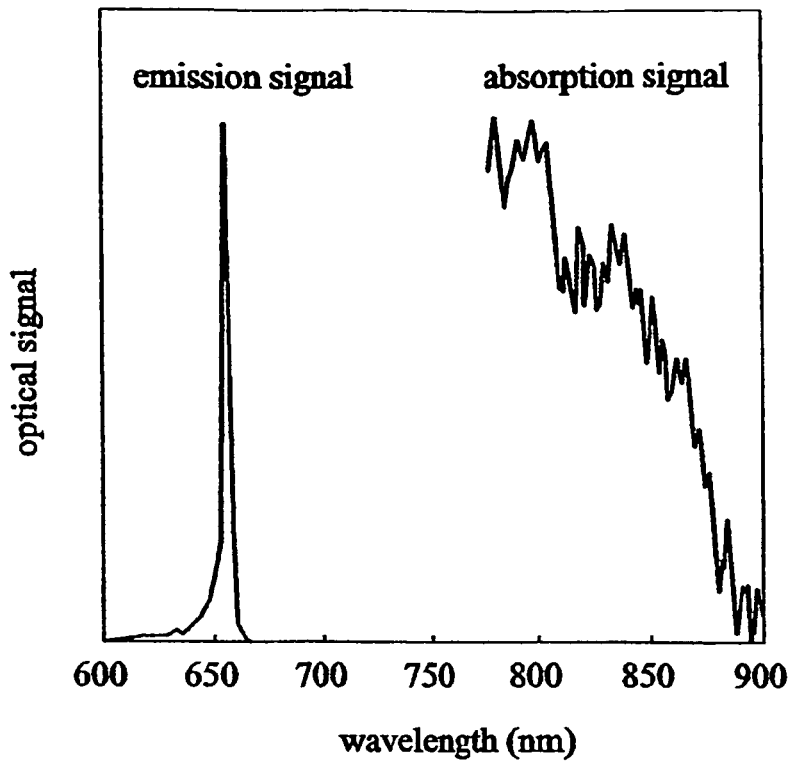
FIG. 6 is a graph showing the light emission/detection spectra of this device.

FIG. 6 shows the emission and detection spectra of a device which we have produced in accordance with the above teachings and shows clearly that the emitted light is unaffected by the absorbing layer, whilst effective detection of light occurs at longer wavelengths, extending up to 890 nm.

By providing the absorbing layer in an undoped region of semiconductor of the device, it is ensured that an electric field exists across the absorbing layer, so that the electron and hole pairs (which are generated upon absorbing the longer-wavelength light) are effectively removed and contribute to the current flow through the device. In this way, an external signal is provided, dependent on the intensity of the received light of longer wavelength.

In a modification of the device of FIG. 2, the device may comprise a resonant cavity LED instead of a VCSEL.

Figure 7:
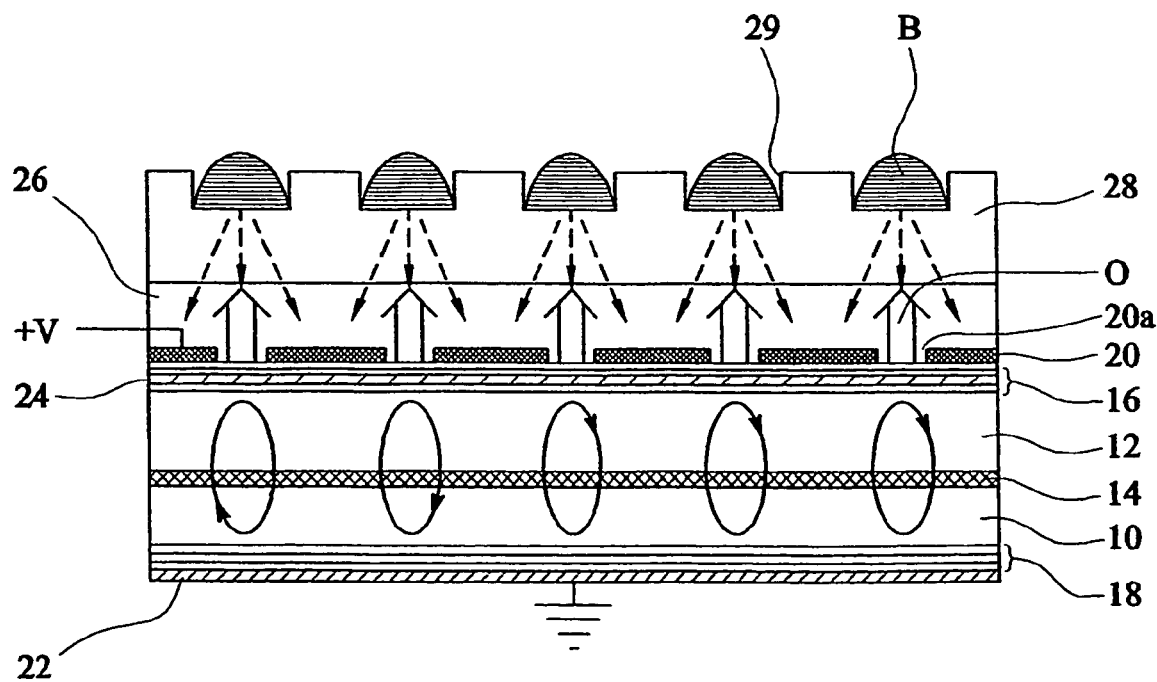
FIG. 7 is a diagrammatic section through a semiconductor emitter/detector device forming a second embodiment of the present invention.
Figure 8:
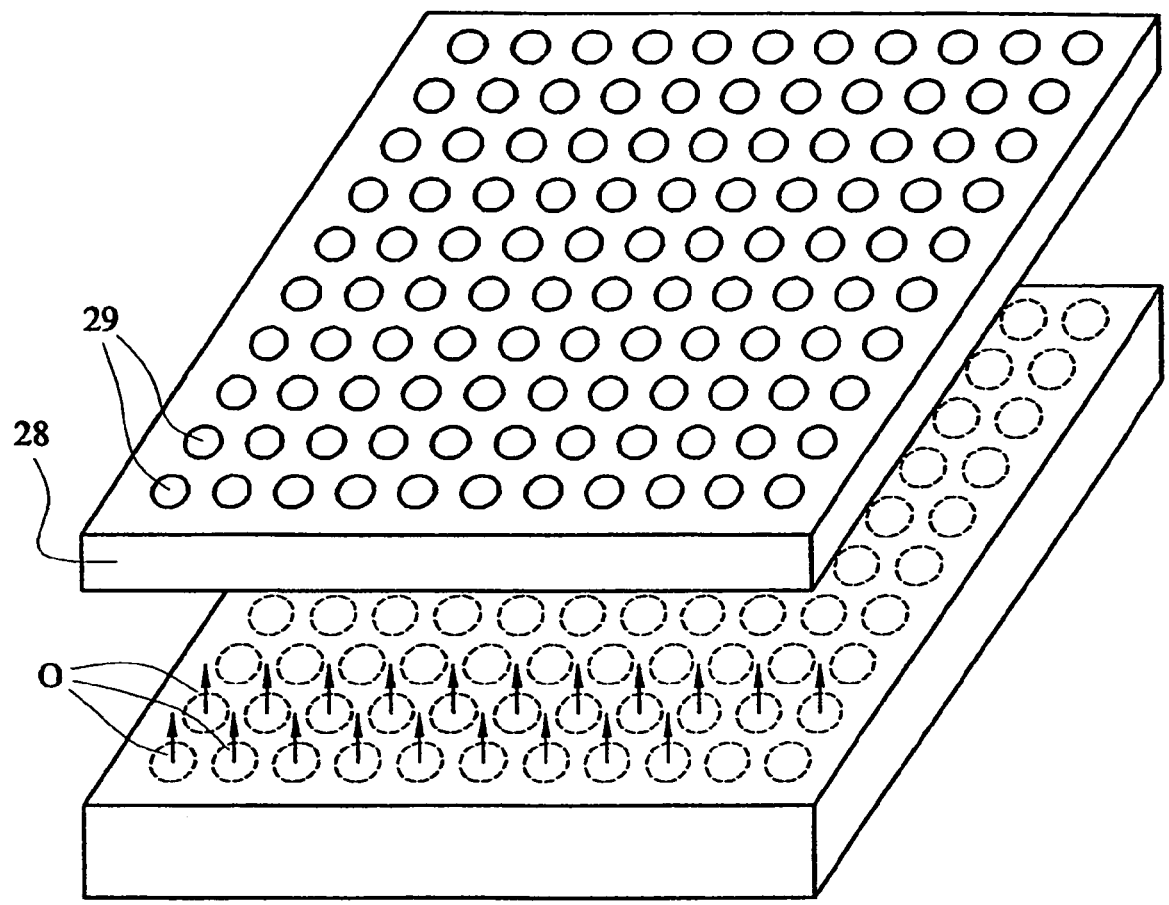
FIG. 8 is a view of the device of FIG. 7.

Referring to FIGS. 7 and 8, there is shown a semiconductor device in the form of a two-dimensional array of vertical-cavity, surface-emitting lasers L, for use in performing an analytical test on a corresponding array of biological or bio-chemical samples B. The device comprises a semiconductor substrate having cavity layers 10,12 and an intermediate gain material layer 14, and upper and lower multi-layer reflectors 16,18: each reflector comprises a plurality of alternating layers of high and low refractive index materials, each layer being a ¼ wavelength thick. The device is provided with an array of electrodes 20 on its upper surface and with a common or ground electrode 22 on its bottom surface. In use, a voltage is applied between each upper electrode 20 and the bottom electrode 22, to provide respective current paths through the device. In each current path, the device is excited to cause local lasing action within the device cavity, the laser output light O being emitted through the spaces or windows 20a between the electrodes 20 on the top surface of the device. It will be appreciated that the arrangement forms a two-dimensional array of lasers.

An interface layer 26 is formed over the upper electrode 20 and upper reflector 16, and a sample-receiving substrate 28 is disposed over the interface layer 26. The upper surface of the sample-receiving substrate 28 is formed with a two-dimensional array of recesses or wells 29, for receiving respective samples B: the wells 29 are aligned with respective windows 20a between the upper electrodes 20 of the device; thus, there is one independent laser for each sample well 29. The sample-receiving substrate 28 may be integrated with the semiconductor device: alternatively, it may comprise a separate component, as shown in FIG. 8, which can be removed and disposed off if desired.

The upper reflector 16 of the device of FIG. 7 includes a layer 24 of narrow bandgap material, forming an absorbing layer for light returned by each sample. The absorbing layer 24 is positioned, within the reflector 16, in the same manner as described with reference to FIGS. 2 to 6.

Light O emitted from each laser is incident on the corresponding sample B, which is marked with a fluorescent dye, thus stimulating the sample to cause emission of light of longer wavelength. Some of this light returns to the respective laser L of the device and is absorbed locally by the absorbing layer 24, with the result of altering the current-voltage characteristic of the respective laser L. A constant voltage source may be connected across each laser L, via its respective upper electrode 20 and the ground electrode 22, and means provided for monitoring the current flow through that laser: alternatively each laser L may be fed from a constant current source, and means provided for monitoring the voltage across that laser.

In a modified form of the embodiment shown in FIG. 7, each laser L may be provided with a photodetector, integrated within the semiconductor device, to receive light D returned from the respective sample B, the absorbing layer 24 being dispensed with. The photodetector of each laser will detect laser light reflected back from the respective sample, or light emitted from the sample in response to stimulation by the laser light. The outputs of the photodetectors are connected to a monitoring circuit.

It will be appreciated that the device of FIG. 2, or the above-described modified form thereof, may comprise an array of resonant cavity LEDs, instead of an array of VCSELs.

In another modified form of the embodiment shown in FIG. 7, again with the absorbing layer 24 dispensed with, the output light from each laser is reflected by the respective sample and returns into the laser, acting to modify the current-voltage characteristic of the laser. A circuit is connected to the electrodes 20 of the lasers, to monitor the current through and/or voltage across each laser.

Figure 9:
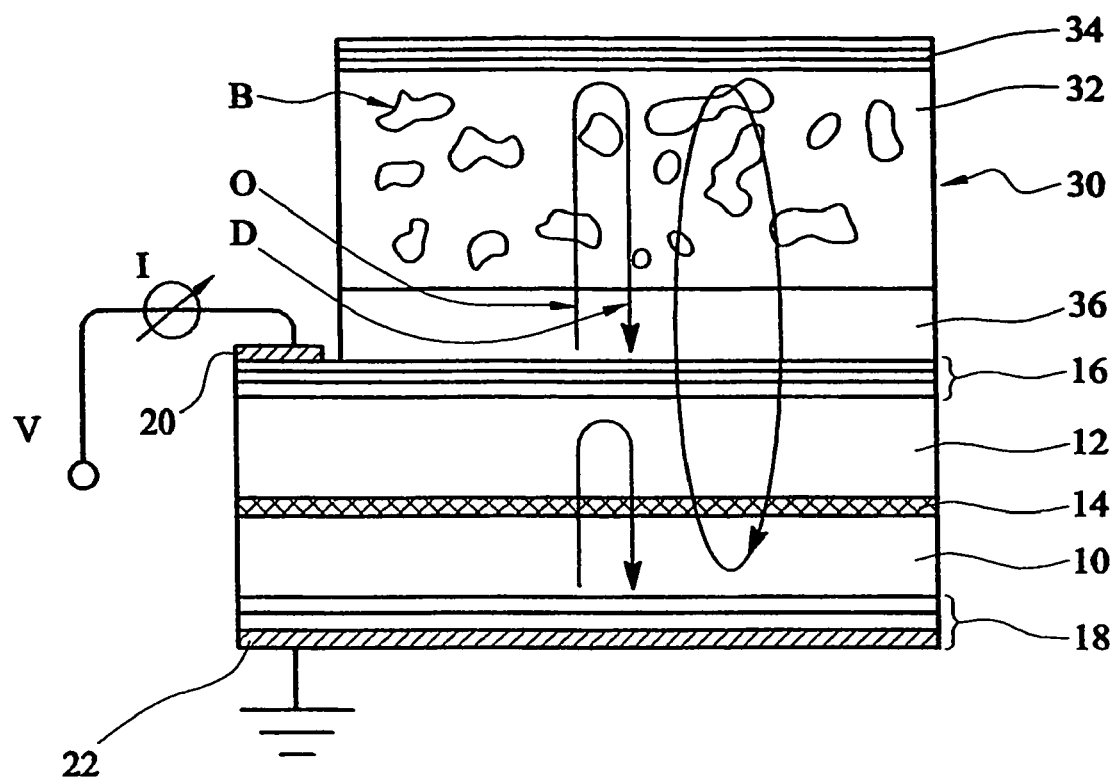
FIG. 9 is a diagrammatic section through a semiconductor emitter/detector device forming a third embodiment of the present invention.

Referring to FIG. 9, there is shown a semiconductor device in the form of a vertical cavity, surface-emitting laser, having a second optical cavity 30 in contact with it, the cavity containing a biological or biochemical sample or including a flow duct for such a sample. The device comprises a semiconductor substrate having cavity layers 10,12 and an intermediate gain material layer 14, and upper and lower multi-layer reflectors 16,18: each reflector comprises a plurality of alternating layers of different materials, respectively of high and low refractive index, each layer being a ¼ wavelength thick. The device is provided with electrodes 20,22 on its top and bottom surfaces: in use, a voltage is applied between these electrodes to provide a current flow through the device, exciting the device to cause lasing within the device cavity and emission of laser output light O through the top surface of the device.

The second optical cavity 30 comprises a container 32 for the sample B, the upper side of the container 32 comprising a multi-layer reflector 34 of construction corresponding to the reflectors 16,18 of the laser device. A transparent spacer 36 is interposed between the underside of the container 32 and the upper surface of the device.

The two optical cavities form a coupled-cavity system, the emitted laser light O being transmitted through the sample B, then reflected, by the reflector 34 of the second cavity, back into the laser device. This return or feedback light D is amplified within the laser device and so modifies its current-voltage characteristic. A circuit is connected to the electrode 20 of the laser, to monitor the current through and/or voltage across the laser.

In a modified form of the embodiment of FIG. 9, the reflector 16 of the device includes a narrow bandgap absorbing layer, in the same manner as described with reference to FIGS. 2 to 6, for absorbing stimulated-emission light from the sample B, of a different wavelength to the laser output.

In this form, the device may comprise a resonant cavity LED, instead of a VCSEL.

As mentioned previously, a semiconductor device in accordance with the present invention may comprise a light emitter element and a photodetector element, both integrated on a single substrate. Either the light emitter or photodetector, or both, may comprise a resonant cavity, in the form either of an LED or a laser. Where the photodetector is intended to detect light of a different wavelength from the light emitted by the light emitter, then it may be desirable for the photodetector to be arranged to respond preferentially to light of the former wavelength, so that it is relatively immune to some of the emitted light being returned, by scattering, to the photodetector. For example, the photodetector element may be provided with a filter layer, at or adjacent its surface, which is relatively opaque to light of the wavelength of the light emitted by the light emitter element of the device, but relatively transparent to light of the wavelength to be detected.

Figure 10:
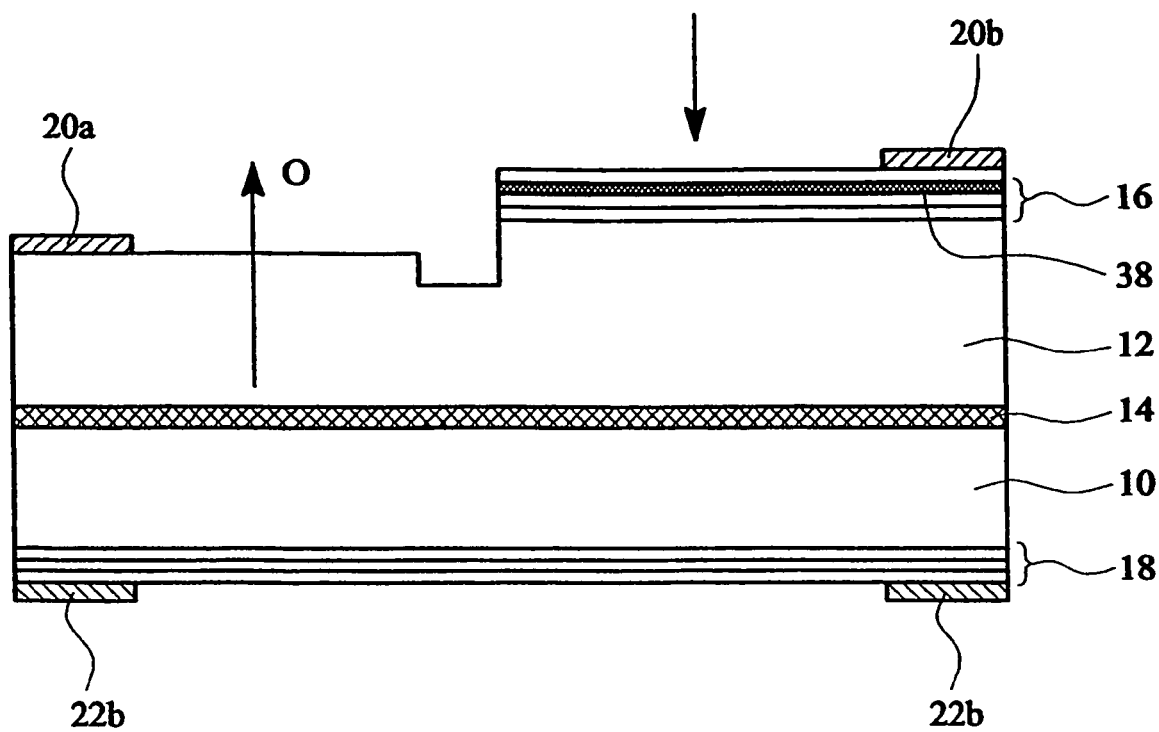
FIG. 10 is a diagrammatic section through a further embodiment of semiconductor emitter/detector device in accordance with the present invention.

FIG. 10 shows a device in which the upper reflector of the photodetector element includes a layer 38 forming an absorption filter blocking any reflected emission light. The device comprises a semiconductor substrate having cavity layers 10, 12 and an intermediate gain material layer 14, and upper and lower multi-layer reflectors 16, 18 each comprising a plurality of alternating layers of high and low refractive index materials, as devised above with reference to FIG. 2, for example. The upper reflector 16 has, however, been etched away over one portion of the substrate, and a trench 40 separates the two portions of the device, to form emitter and photodetector elements. The device is provided with electrodes 20*a*, 22*a* and 20*b*, 22*b* on the top and bottom surfaces of the emitter and photodetector elements of the device, a forward bias being applied across electrodes 20*a*, 22*a* and a reverse bias being applied across electrodes 20*b*, 22*b*. In use of the device, light O of a first wavelength is emitted from the upper surface of the emitter element of the device: any reflected light of this wavelength, incident on the photodetector element, is filtered out by the absorbing layer 38, whilst light of e.g. longer wavelength passes through this layer and is detected within the photodetector element. As described previously, a constant-voltage source may be connected across the photodetector electrodes 20*b*, 22*b* and a circuit provided to monitor the current, or instead a constant-current source is connected across the electrodes 20*b*, 22*b* and a circuit provided to monitor the voltage between them. Conveniently, the trench 40 may be annular in form, encircling a central emitter element of relatively small diameter (perhaps of the order of 10 microns), and itself encircled by a photodetector element of relatively large diameter (perhaps of the order of 500 microns).

Preferably the reverse bias applied to the photodetector element places this diode close to its breakdown point, so that, in use, avalanche photo-detection occurs: a substantially increased detection signal (of the order of a thousand-fold increase) can accordingly be achieved.

Figure 11:
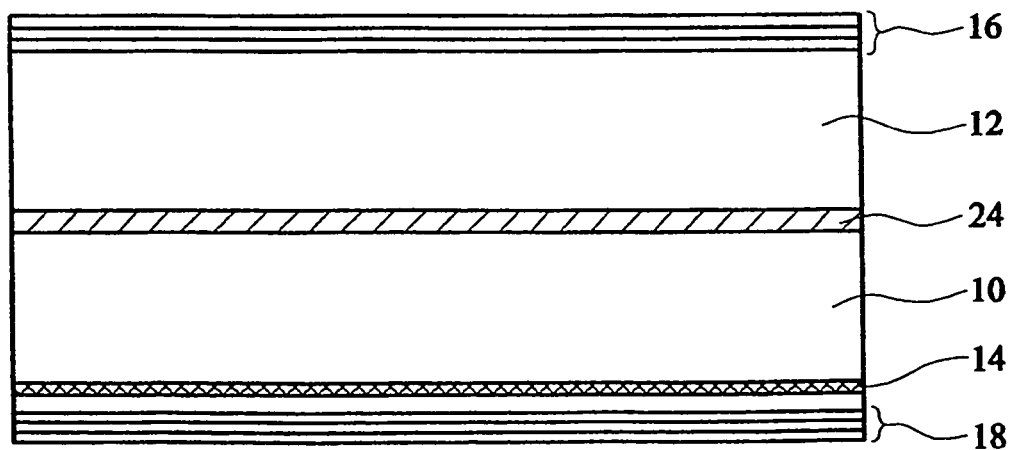
FIG. 11 is a diagrammatic section through a modification to the device of FIG. 2.

It will be noted that, in the device of FIG. 2 for example, the light-emitting layer 14 is disposed centrally between the upper and lower reflectors and the cavity is resonant at the wavelength of the emitted light. Instead, and referring to FIG. 11, the cavity may be resonant at the wavelength of light to be detected, in which case the layer 24, which is absorbing to the light to be detected, is disposed centrally between the upper and lower reflectors 16,18: further, the emitting layer 14 is disposed adjacent either the upper or lower reflector.

Whilst in the embodiment of FIGS. 7 and 8, for example, the substrate comprises a plurality of light emitters arranged in a two-dimensional array, these may instead be arranged in a linear array, for example adjacent a passage for the flow of fluid, arranged to examine the fluid at successive points along its flow path.

It will be appreciated that, in each of the above-described embodiments, the monitoring means may comprise a circuit part of which is integrated on the semiconductor substrate of the device.

Figure 12:
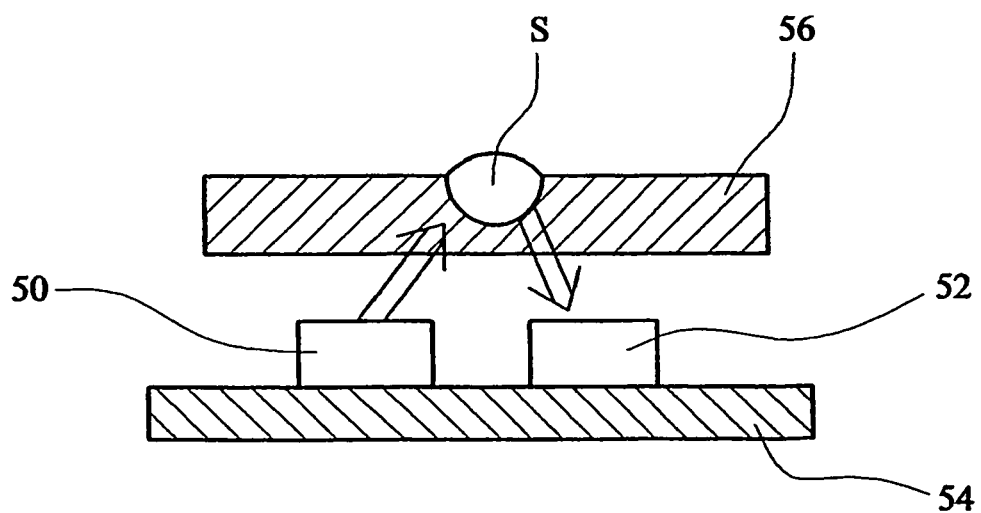
FIG. 12 is a schematic cross-section through a yet further embodiment of device in accordance with the invention.

Referring to FIG. 12 of the drawings, there is shown a device for the analysis of a biological or other sample, the device comprising a semiconductor light emitter 50 and a semiconductor photodetector 52 mounted side-by-side on a substrate 54. A sample-carrier 56 is positioned over the light emitter 50 and photodetector 52 and comprises a transparent substrate the upper surface of which is formed with a recess or well to receive the sample S to be analysed or tested. The substrate 56 may form a permanent part of the device, or it may be removable and replaceable.

The device is arranged so that the light emitted by the emitter 50 is incident on the sample S and the photodetector 52 picks up light returned from the sample S. In the sample shown in FIG. 12, the light emitter 50 comprises a resonant-cavity, light emitting diode (RCLED) with an emission peak at a wavelength of 650 nm: the photodetector comprises an identical device except that it has an emission peak at 670 nm and is used with a reverse voltage bias (so as to act as a photodetector rather than light emitter). In use of the device, the sample S is marked with a fluorescent dye: accordingly, the light of 650 nm wavelength which is incident on the sample, from the emitter 50, stimulates the sample to cause emission of light of the longer-wavelength, which is picked up by the photodetector 52.

We have made and tested light emitters and photodetectors in the form of GaInP crystals having multiple-layer Bragg reflectors to produce circular beams perpendicular to their surfaces. By control of the thickness of these crystals, we formed two devices with emission peaks at 650 nm and 670 nm, respectively: the first such device is used as the emitter 50 and the second device, under reverse bias, as the photodetector 52.

Figure 13:
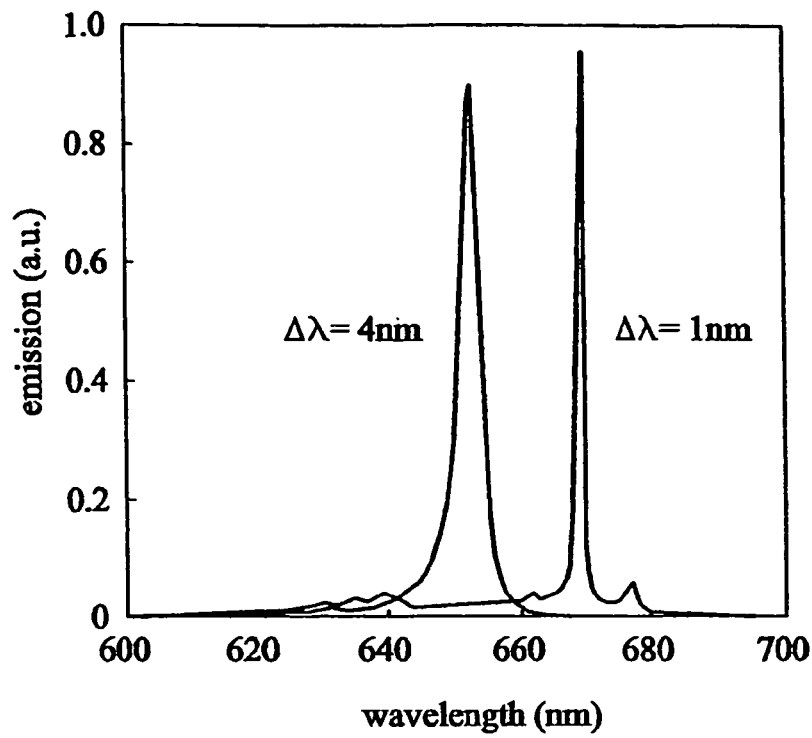
FIG. 13 is a graph showing the emission spectra of two light emitters used in the device in FIG. 12.

FIG. 13 shows the emission spectra of the two devices, one having a peak at 650 nm and the other a peak at 670 nm.

Figure 14:
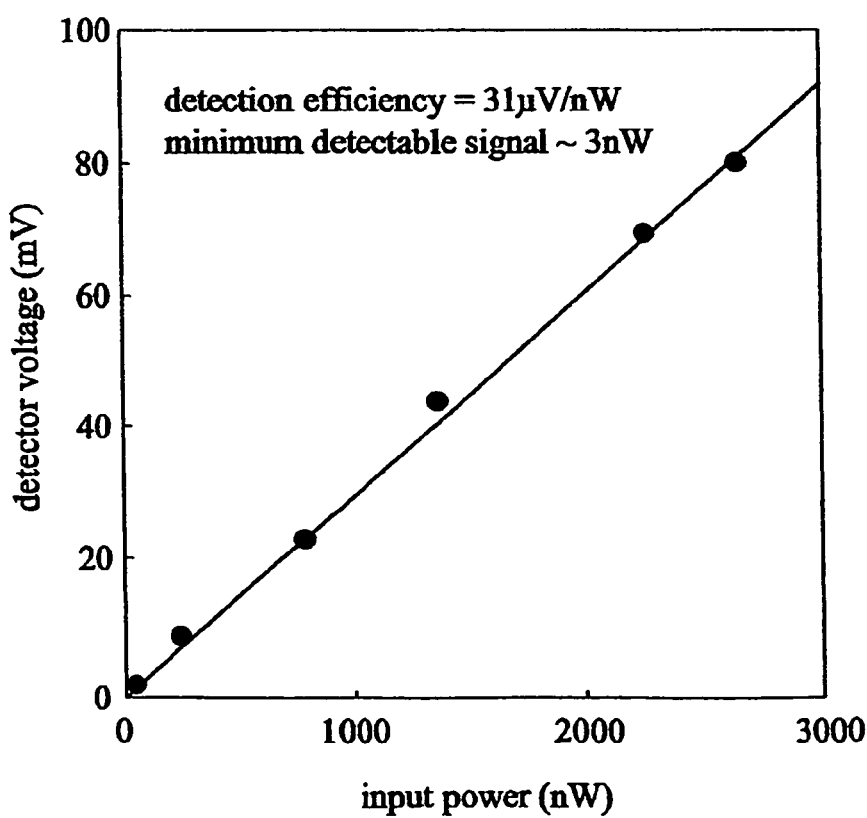
FIG. 14 is a plot showing the detection performance of one of the light emitters of the device of FIG. 12, used with reverse bias to act as a photodetector.

FIG. 14 shows the detected photovoltage, of the photodetector 52, in response to an optical signal. We found detection possible down to a noise floor of 3 nW: for a typical fluorescent dye with a radiative lifetime of 5 ns, this corresponds to the detection of the fluorescent emission from just 51 molecules, demonstrating the extremely high sensitivity of the photodetector.

It will be appreciated that the device described with reference to FIG. 12 also comprises a battery power source for applying forward and reverse voltages to the emitter 50 and photodetector 52, respectively: the device further comprises a circuit for measuring the voltage or current output of the photodetector.

The invention claimed is:

1. A device comprising:
   a semiconductor substrate arranged for emitting light for incidence on an element and also responsive to light received from said element; and
   means for monitoring a characteristic of the device which varies in dependence upon said light received from said element;
   wherein the device includes a resonant cavity light emitting element integrated as part of said substrate for emitting light of a first wavelength range, comprising a reflector through which light is emitted, the reflector comprising a plurality of alternating layers of high and low refractive index material, a layer of absorbing material being incorporated into or associated with said reflector, said absorbing layer realized from a bandgap material that absorbs light of a second wavelength range different from said first wavelength range while not absorbing light of said first wavelength range.

2. A device as claimed in claim 1, arranged such that said received light affects an electrical property thereof and so alters its current-voltage characteristic, said monitoring means being arranged to monitor said current-voltage characteristic.

3. A device as claimed in claim 1, comprising a light emitter element and a photodetector element, both integrated on said substrate.

4. A device as claimed in claim 3, in which said light emitter element comprises a resonant cavity element.

5. A device as claimed in claim 3, in which said photodetector element is arranged to detect light of a different wavelength from the light emitted by said light emitter element.

6. A device as claimed in claim 5, in which said photodetector element is arranged to respond preferentially to said different-wavelength light and is relatively non-responsive to light of the wavelength emitted by said light emitter element.

7. A device as claimed in claim 6, in which said photodetector element is provided with a wavelength-selective filter layer, at or adjacent its light-receiving surface.

8. A device as claimed in claim 7, in which said photodetector element comprises a resonant cavity and said filter layer is provided in an upper reflector of said photodetector element.

9. A device as claimed in claim 8, in which said semiconductor substrate comprises said resonant cavity between upper and lower reflectors, a region of said upper reflector being removed to form said emitter element, another region of said substrate forming said photodetector element and including said filter layer in its said upper reflector.

10. A device as claimed in claim 3, in which said photodetector element comprises a diode arranged for a reverse bias applied to it to place said diode close to its breakdown point so that, in use, avalanche photo-detection occurs.

11. A device as claimed in claim 1, comprising a resonant cavity light emitting device, having a secondary optical cavity disposed over a light-emitting surface thereof, to form a coupled-cavity system, said secondary optical cavity including a chamber or flow duct for a sample.

12. A device as claimed in claim 1, in which said absorbing layer is disposed in an undoped semiconductor region of said substrate.

13. A device as claimed in claim 12, in which said absorbing layer is disposed between two groups of alternating high and low refractive index materials which form said reflector.

14. A device as claimed in claim 1, comprising an array of resonant cavity light emitting elements integrated as part of said substrate, each resonant cavity light emitting element having said reflector and said layer of absorbing material, said array of resonant cavity light emitting elements arranged to operate independently of each other and with said monitoring means arranged for monitoring a characteristic of each given light emitting element independently of the others.

15. A device as claimed in claim 14, in which said light emitting elements are arranged in a linear array.

16. A device as claimed in claim 14, in which said light emitting elements are arranged in a two-dimensional array.

17. A device as claimed in claim 1, in which said light emitting element comprises one of a resonant cavity laser element and a resonant cavity LED element.

* * * * *